United States Patent
McClurg

(10) Patent No.: US 10,226,318 B2
(45) Date of Patent: Mar. 12, 2019

(54) METHOD OF TREATING URINARY INCONTINENCE BY IMPLANTING A TUBE PROVIDING A PRESSURE-REGULATING STORAGE COMPARTMENT

(71) Applicant: Coloplast A/S, Humlebaek (DK)

(72) Inventor: Steven McClurg, Brooklyn Park, MN (US)

(73) Assignee: Coloplast A/S, Humlebaek (DK)

(*) Notice: Subject to any disclaimer, the term of this patent is extended or adjusted under 35 U.S.C. 154(b) by 0 days.

(21) Appl. No.: 15/727,643

(22) Filed: Oct. 9, 2017

(65) Prior Publication Data
US 2018/0028300 A1 Feb. 1, 2018

Related U.S. Application Data

(62) Division of application No. 13/911,089, filed on Jun. 6, 2013, now Pat. No. 9,814,554.

(30) Foreign Application Priority Data

Jul. 11, 2013 (EP) .................................. 13176087

(51) Int. Cl.
*A61F 2/00* (2006.01)
*A61M 25/00* (2006.01)
*A61B 17/00* (2006.01)

(52) U.S. Cl.
CPC .... *A61F 2/004* (2013.01); *A61B 2017/00805* (2013.01); *A61F 2/0031* (2013.01); *A61F 2/0036* (2013.01); *A61M 2025/0024* (2013.01); *Y10S 128/25* (2013.01)

(58) Field of Classification Search
CPC ...... A61F 2/004; A61F 2/0036; A61F 2/0031; A61M 2025/0024; Y10S 128/25; A61B 2017/00805

See application file for complete search history.

(56) References Cited

U.S. PATENT DOCUMENTS

| 4,994,020 A * | 2/1991 | Polyak ................... A61F 2/004 128/DIG. 25 |
| 4,995,380 A * | 2/1991 | Maerzke ................... A61F 2/26 600/40 |
| 6,162,238 A * | 12/2000 | Kaplan ................. A61F 2/0036 604/9 |
| 2012/0184980 A1 * | 7/2012 | Anderson ............. A61F 2/0036 606/192 |
| 2013/0303841 A1 * | 11/2013 | Fogarty ................... A61F 2/004 600/31 |

* cited by examiner

*Primary Examiner* — Kaylee R Wilson
(74) *Attorney, Agent, or Firm* — Coloplast Corp., Coloplast A/S; Nick Baumann

(57) ABSTRACT

A method of treating urinary incontinence includes providing a device having a cuff configured to coapt a urethra of a patient in treating diagnosed urinary incontinence, a pump, and a tube attachable between the cuff and the pump. The method includes providing the tube with a first lumen separated from a second lumen by a wall internal to the tube, and providing at least a portion of an exposed exterior wall of the second lumen to expand to provide the second lumen with an inflatable storage compartment.

13 Claims, 10 Drawing Sheets

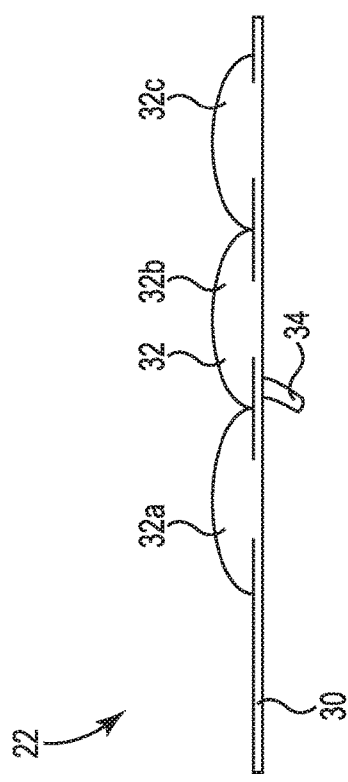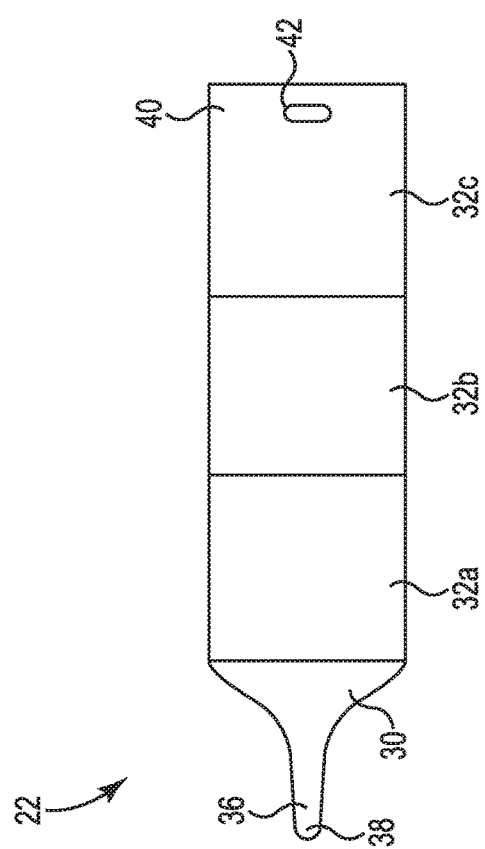

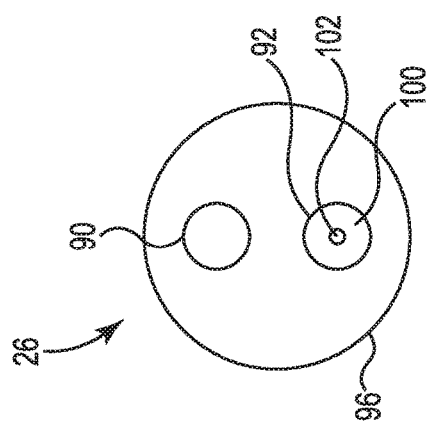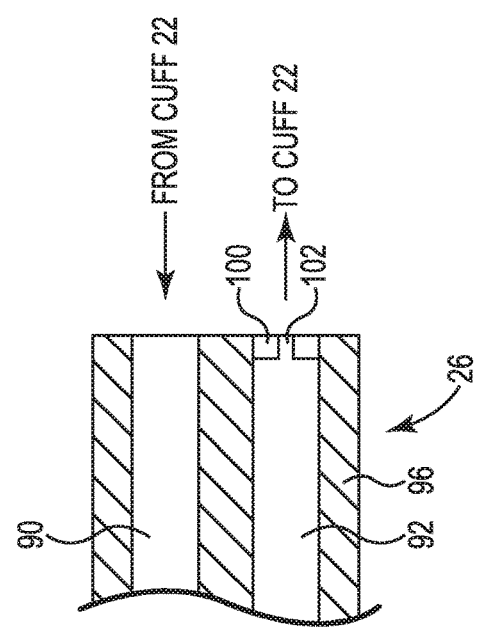

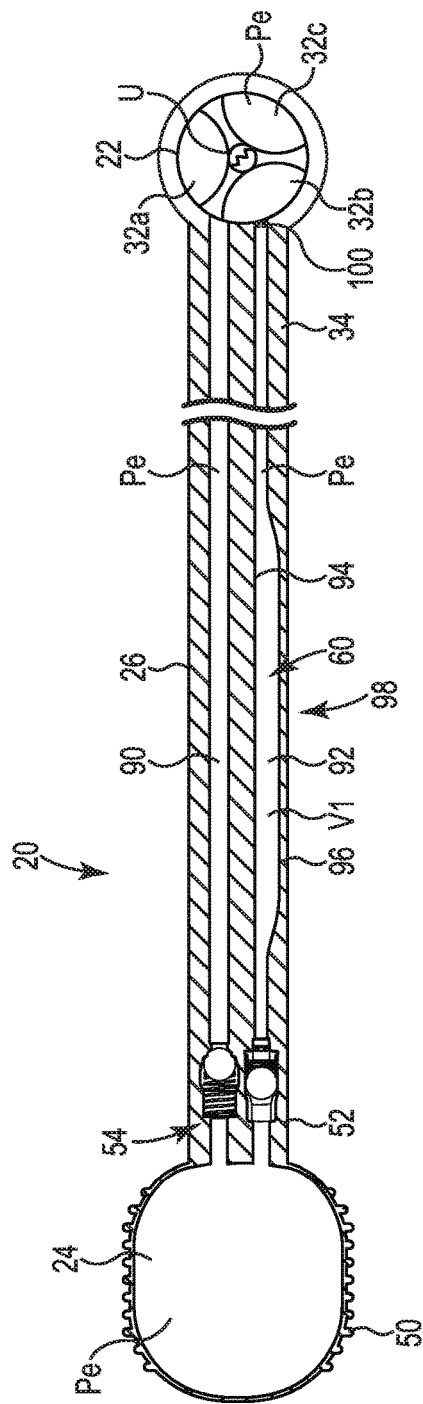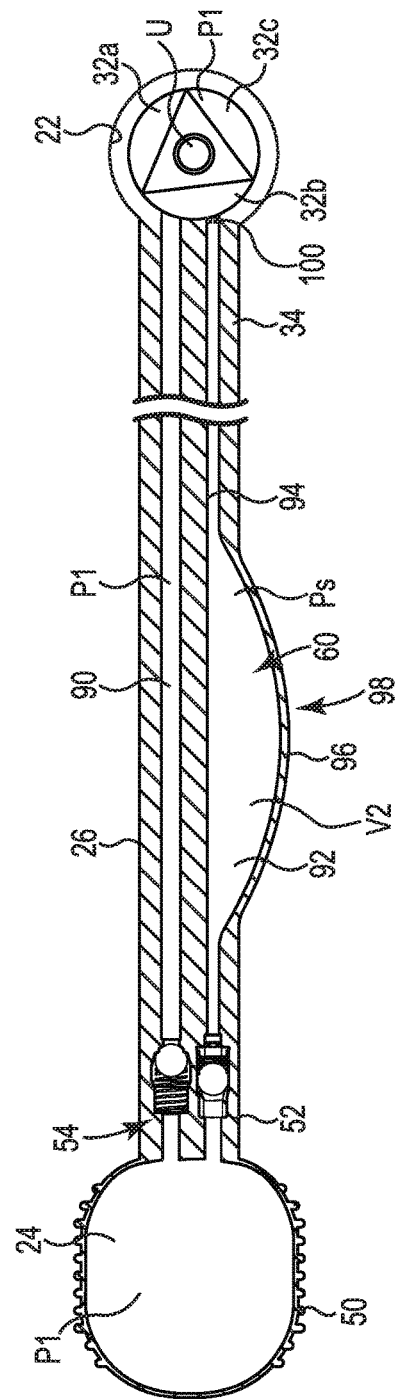

METHOD OF TREATING URINARY INCONTINENCE BY IMPLANTING A TUBE PROVIDING A PRESSURE-REGULATING STORAGE COMPARTMENT

BACKGROUND

Urinary incontinence affects about 200 million people worldwide and about 25 million people in the US. Urinary incontinence is generally more prevalent in women than in men.

Urinary incontinence in women can be associated with a prolapse of one or more pelvic organs, which can arise from a weakness in the tissues/muscle of the pelvic floor. Urinary incontinence in men can arise after surgical treatment of the prostate glade, which treatment can include removal or weakening of the prostatic sphincter associated with the urinary urethra.

One treatment for urinary incontinence includes placing an artificial sphincter around a portion of the urethra. The artificial sphincter has a closed position that selectively prevents the flow of urine through the urethra, thus providing the user with a comfortable, continent state. The artificial sphincter can be activated to an open position by the user, which opens the urethra and allows the user to selectively pass urine.

Surgeons and patients would welcome advances in the treatment of urinary incontinence.

SUMMARY

One aspect provides an artificial urinary sphincter (AUS) system including a cuff, a pump, and a single tube that provides the system with a storage compartment. The system is a closed system having liquid in the cuff that inflates the cuff to coapt the urethra. The pump is operable to move the liquid out of the cuff to provide the cuff with a deflated state that allows the urethra to open and pass urine. The single tube stores the energy of the closed system and is operable to store the liquid moved out of the cuff. In this manner, the single tube replaces the role of and does away with the extra component of a pressurized balloon reservoir.

One aspect provides an artificial urinary sphincter (AUS) system including a cuff, a pump, and a tube that provides the system with an inflatable storage compartment. The cuff is sized to be placed around a urethra of a user and is configured to coapt the urethra in treating urinary incontinence. The pump is configured to move liquid out of the cuff to provide the cuff with a collapsed state that allows the urethra to pass urine. The tube is connected between the cuff and the pump and includes a first lumen separated from a second lumen by a wall internal to the tube. The second lumen includes an exposed exterior wall and at least a portion of the exposed exterior wall of the second lumen is configured to expand to provide the second lumen with the inflatable storage compartment.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily drawn to scale relative to each other. Like reference numerals designate corresponding similar parts.

FIG. 2 is a side view and FIG. 3 is a top view of one embodiment of a cuff of the AUS system illustrated in FIG. 1.

FIG. 9 is an end view and FIG. 10 is a cross-sectional view of one embodiment of an end of the tube that is connected to the cuff of the AUS system illustrated in FIG. 1.

FIG. 11A is a cross-sectional view of the AUS system illustrated in FIG. 1 in a rest or equilibrium state configured to coapt a urethra of a user.

FIG. 11B is a cross-sectional view of the AUS system illustrated in FIG. 1 in an activated state configured to allow the urethra of the user to open and pass urine.

DETAILED DESCRIPTION

Figure 1:
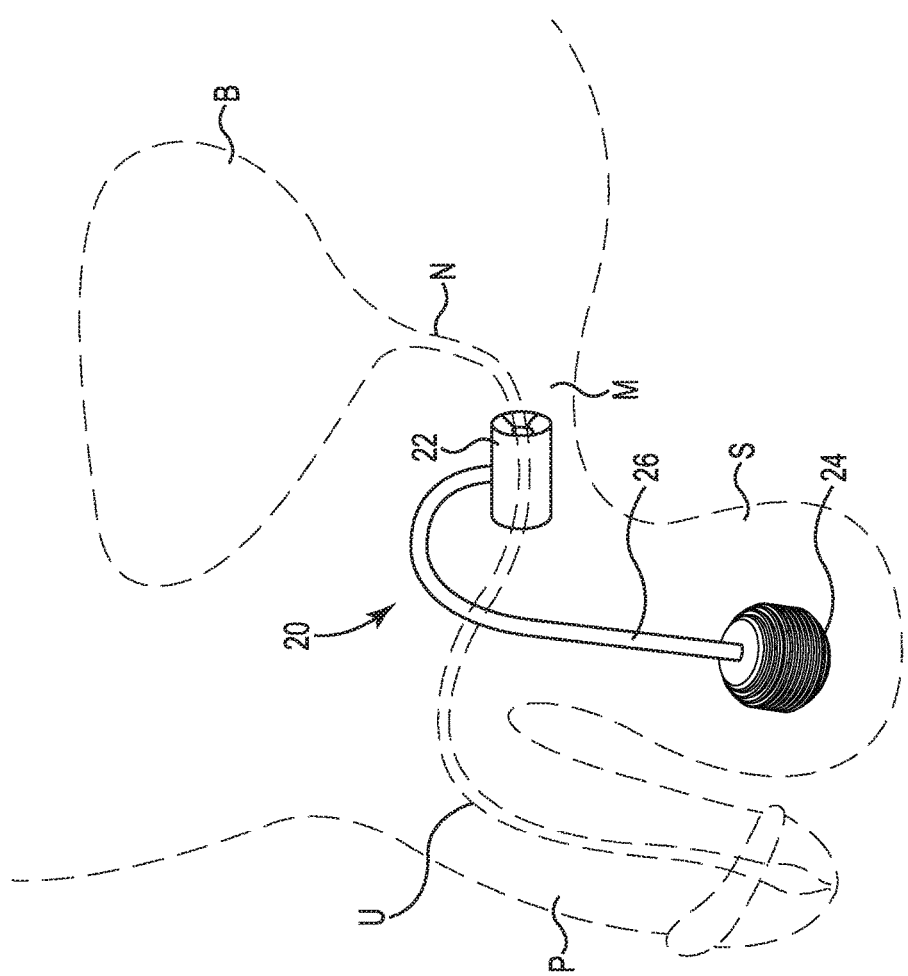
FIG. 1 is a perspective view of one embodiment of an artificial urinary sphincter (AUS) system implanted in the urogenital region of a male patient.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft tissue, which includes dermal tissue, sub-dermal tissue, ligaments, tendons, or membranes. As employed in this specification, the term "tissue" does not include bone.

As employed in this specification, the term "end" means endmost or the very end point of the subject being described, and the term "end portion" means that segment that is immediately adjacent to the end of the subject being described.

One urinary control system that has found favor with the medical community includes three components cooperatively attached with kink-resistant tubing: an occlusive cuff, a control pump, and a pressure-regulating balloon reservoir. The cuff is implanted around the urethra. The control pump is implanted in the scrotum of a male user. The pressure-regulating balloon reservoir is implanted in the prevesical space, for example through a suprapubic incision followed by dissection of the rectus fascia and a spreading of the linea alba. The three components are filled with liquid (saline) to provide a liquid-filled closed system maintained at an equilibrium pressure that closes the cuff around the urethra. When the user wishes to void, he squeezes and releases the pump several times to move fluid from the cuff into the pressure-regulating balloon reservoir. The cuff "deflates" and opens, which allows the urethra to open and pass urine. The pressure-regulating balloon reservoir, having been pressurized to a pressure above the equilibrium pressure by action of the pump, eventually automatically re-pressurizes the cuff to the equilibrium pressure over the course of several minutes to again inflate the cuff and coapt the urethra.

Embodiments described in this application provide a system that is provided with a conduit extending between a cuff and a pump of the system, where the conduit includes an inflatable storage compartment that expands to retain/ store the volume of liquid maintained in the closed system. The system can be adapted to provide treatment for urinary incontinence in which the conduit extends between a pump and an artificial urinary sphincter of the system. Separately, the system can be adapted to provide treatment for erectile dysfunction in which the conduit extends between a pump and an inflatable penile cylinder of the system. In any regard, the system described in this patent application is characterized by the absence of a pressure-regulating balloon reservoir that ordinarily stores the liquid and pressurizes the closed system. In one embodiment, the system described by the embodiments has two components cooperatively attached with the conduit, namely a cuff and a pump.

The exemplary AUS system described in this patent application is suited for use both in female patients and in male patients, where the cuff is placed around a portion of the urethra. Female patients will have the pump component implanted in one of the labia or in an abdominal area. Male patients will have the pump component implanted in the scrotum.

One advantage of the two-component AUS system described in this patent application is that the pressure-regulating balloon reservoir is done away with and its function is provided by the newly described conduit connected between the cuff and the pump. Thus, fewer components are implanted into the user, which provides a smaller AUS device that is easier to implant and offers a quicker recovery time from the implantation surgery.

FIG. 1 is a perspective view of one embodiment of an artificial urinary sphincter (AUS) system 20 illustrated as implanted in the environment of the male urogenital region. Although the illustrated environment is that of a male user, the system is also suited for implantation into a female user.

The AUS system 20 includes a cuff 22 that is sized to be placed around a urethra U, a pump 24 that is sized for placement within the scrotum S, and a tube 26 or conduit 26 that is attached between the cuff 22 and the pump 24. The AUS system 20 is characterized by the absence of a separate reservoir that is ordinarily provided to retain the liquid that is transferred to inflate the cuff 22. Embodiments of the AUS system 20 configure the tube 26 or the conduit 26 to provide an expandable and inflatable storage compartment that stores liquid transferred out of the cuff 22 when the cuff 22 is deflated.

The AUS system 20 can be referred to as a two component system, where the two components include the cuff 22 and the pump 24. In contrast, a typical three component system would include a cuff attached to a separate reservoir and a pump attached to the cuff.

The cuff 22 is implanted around the bulbous urethra or around the portion of the urethra descending from the bladder neck N. The cuff 22 is sized to allow placement as close to the bladder B as possible (desired by some surgeons), or positioned distal the bladder neck N as suitably determined by the surgeon. As illustrated in FIG. 1, the cuff 22 is implanted around the urethra U at a location where the urethra U transitions from a vertical orientation communicating with the bladder B to a horizontal orientation extending to the penis P, which corresponds to the area of the urogenital region associated with an increased level of muscle M mass. The cuff 22 is generally about 2 cm wide and have varying lengths suited to different anatomical sizes, where the lengths are provided in a range between 4-11 cm.

The pump 24 is typically implanted within the scrotum S, which provides access to the pump 24 by the user. Other locations for placement of the pump 24 are also acceptable.

The tube 26 is connected between the cuff 22 and the pump 24, and when implanted thus extends from a location in the scrotum S to a location distal the bladder B.

FIG. 2 is a side view and FIG. 3 is a top view of one embodiment of the cuff 22. The cuff 22 includes an expanding bladder portion 32 attached to a base 30. A connector 34 is provided on the base 30 for connection with the tube 26 (FIG. 1), and the connector 34 communicates with the bladder portion 32. In one embodiment, the expanding bladder portion 32 is provided as a series of segments or pillows 32*a*, 32*b*, 32*c* that are configured to expand and inflate as liquid is directed into the cuff 22 through the connector 34. In one embodiment, three of the segments or pillows are provided to allow the base 30 to be bent/folded or directed around the circumference of the urethra such that when the pillows 32 expand, substantially uniform pressure is applied to the urethra. The bladder portion 32 may include more than three or fewer than two segments or pillows.

In one embodiment, the base 30 extends from a first end portion 36 provided with a tab 38 to a second opposing end portion 40 provided with a slot 42. Inserting the tab 38 into the slot 42 forms the cuff 22 into a substantially circular configuration configured for encircling the urethra of the user. Movement of liquid through the connector 34 (for example by the pump 24 shown in FIG. 1) expands or inflates the bladder portion 32, which is useful in inflating the cuff 22 to coapt the urethra to provide the user with a continent state.

Figure 4:
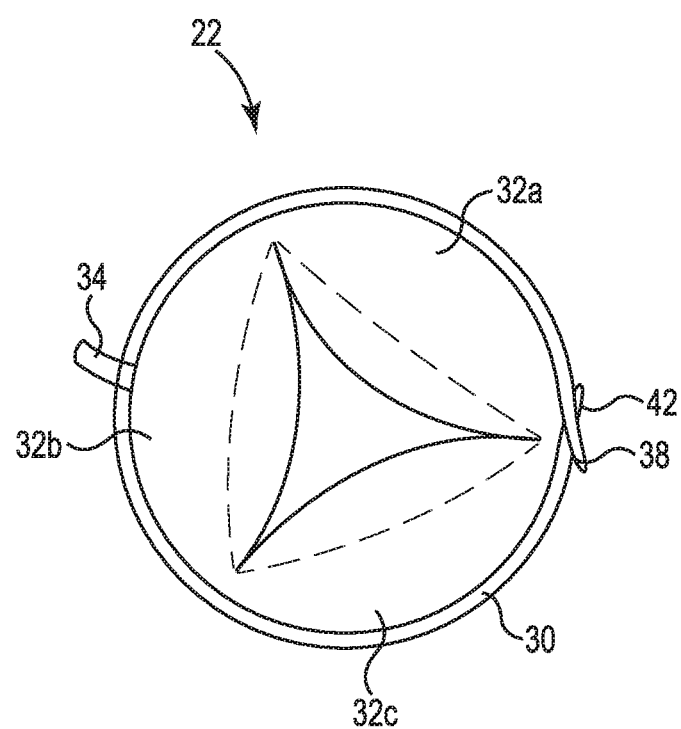
FIG. 4 is an end view of the cuff illustrated in FIG. 2 as assembled and showing a deflated and an inflated configuration.

FIG. 4 is an end view of the cuff 22 with the tab 38 inserted into the slot 42 to form the cuff 22 into a substantially circular shape. The cuff 22 may thus be manipulated for placement around the urethra. When the cuff 22 is deflated (as illustrated by the dotted lines), the bladder portion 32 is retracted to remove or diminish pressure applied to the urethra, which allows the urethra to open and pass urine. In contrast, when the cuff 22 is inflated (as illustrated by the solid lines), the bladder portion 32 expands to apply pressure against the urethra to coapt the urethra and provide the user with a comfortable, continent state.

The cuff 22 is generally fabricated from synthetic material that is suitable for implantation into the human body and configured to retain a volume of liquid (for example when the bladder portion 32 of the cuff 22 is inflated). Suitable materials for fabricating the cuff 22 include silicone, flexible block copolymers, polyolefin, polybutylene, polyurethane, or mixtures or suitable copolymers of the synthetic materials.

Figure 5:
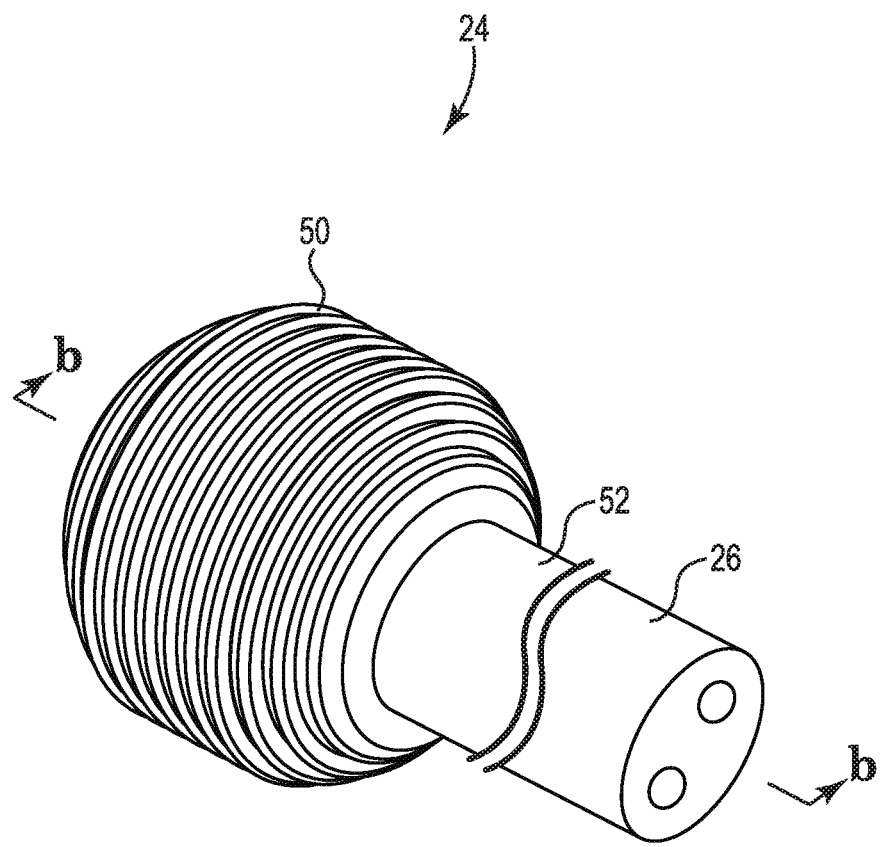
FIG. 5 is a perspective view of one embodiment of a pump of the AUS system illustrated in FIG. 1.

FIG. 5 is a perspective view of the pump 24. The pump 24 includes a bulb 50 connected to a housing 52 that encloses one or more valve assemblies 54 (see FIG. 6). In one embodiment, the valve assemblies 54 are provided as a component of the pump 24. In an alternate and acceptable embodiment, the valve assemblies 54 are integrated with and provided as a component of the tube 26.

Figure 6:
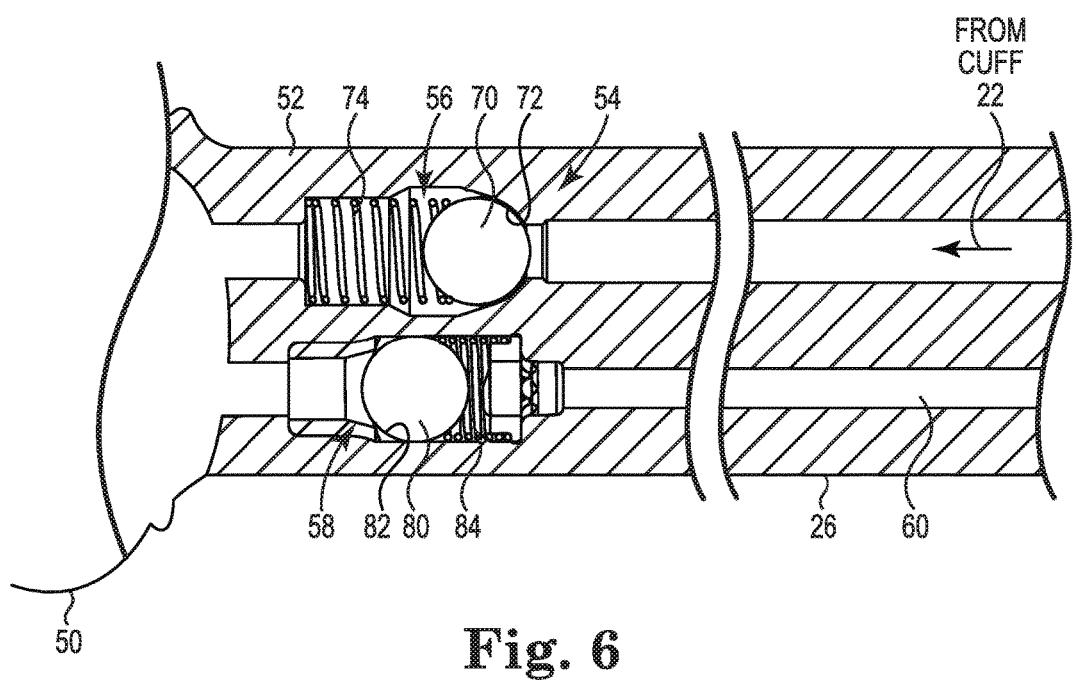
FIG. 6 is a cross-sectional view of one embodiment of the pump illustrated in FIG. 5.

FIG. 6 is a cross-sectional view of the pump bulb 50 and the housing 52. In one embodiment, the valve assemblies 54 include an intake valve assembly 56 and an exhaust valve assembly 58. The intake valve assembly 56 is configured to allow liquid to move out of the cuff 22 (FIG. 1) and into the bulb 50. The exhaust valve assembly 58 is configured to open when the bulb 50 is squeezed or pressurized, which drives the liquid out of the bulb 50 and into a storage compartment 60 that is provided within the tube 26.

In one embodiment, the intake valve assembly 56 includes a ball 70 that is biased against a valve seat 72 by a spring 74. Compressing and releasing the bulb 50 will create a local low pressure (suction) that will draw liquid from the cuff 22 across the valve seat 72, around the ball 70, and into the bulb 50. Subsequent repeated pressing of the bulb 50 will drive the liquid from the bulb 50 through the exhaust valve assembly 58.

In one embodiment, the exhaust valve assembly 58 includes a ball 80 that is biased against a valve seat 82 by a spring 84. Pressure created in the bulb 50 will cause the liquid ejected from the bulb 50 to force the ball 80 off of the valve seat 82 and drive the liquid into the storage compartment 60.

In one embodiment, the intake valve assembly 56 and the exhaust valve assembly 58 are each suitably provided as a one-way valve assembly. In one embodiment, the tube 26 includes a first one-way valve assembly 56 that is configured to allow liquid to flow from the cuff 22 to the pump 24, and a second one-way valve assembly 58 that is configured to allow the liquid to flow from the pump 24 and into the storage compartment 60. A bleeder valve (FIGS. 9 and 10) is configured to allow the liquid to subsequently and gradually flow from the second lumen 92 back into the cuff 22. Other suitable valve assemblies that allow liquid to selectively flow from the cuff 22, into the bulb 50, and into the storage compartment 60 are also acceptable.

In one embodiment, the tube 26 is attachable to the pump 24, for example after the pump 24 and the cuff 22 (FIG. 1) are implanted.

In one embodiment, the tube 26 and the pump 24 are integrated as a monolithic one-piece assembly.

The pump 24 is suitably fabricated from synthetic materials such as those materials identified above for the cuff 22. One suitable material for fabricating the pump 24 is silicone.

Figure 7:
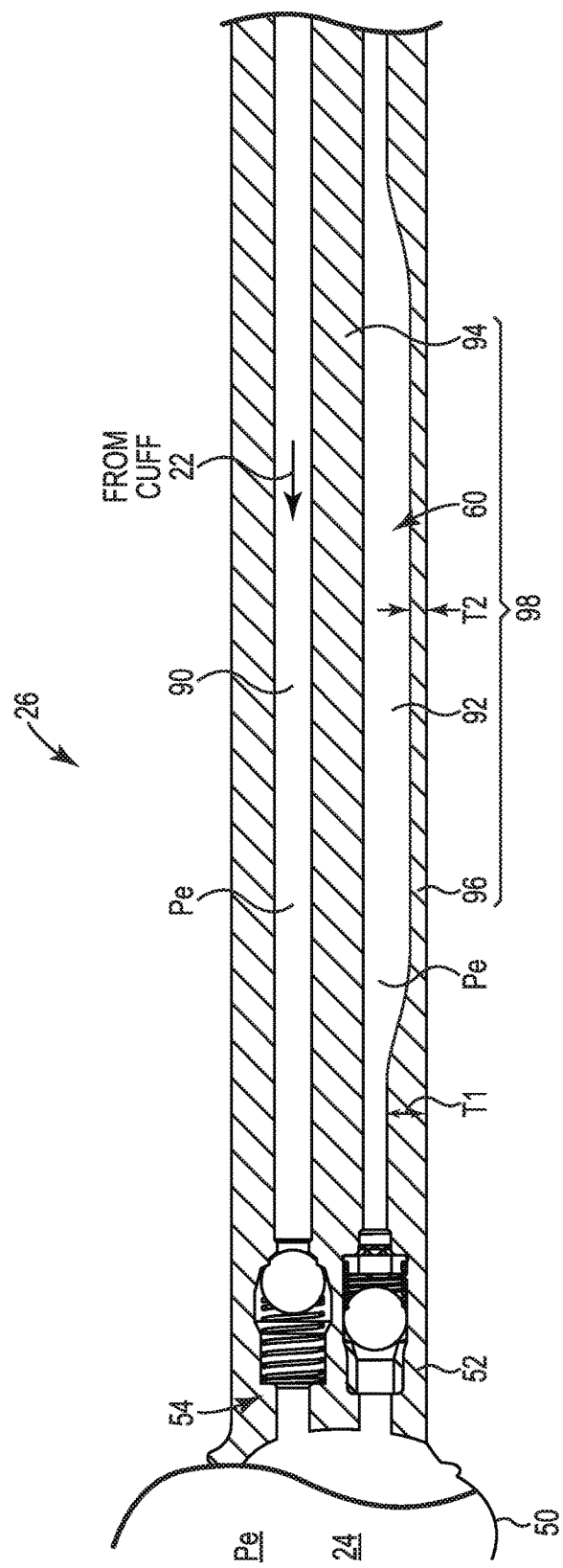
FIG. 7 is a cross-sectional view of one embodiment of a tube of the AUS system illustrated in FIG. 1.

FIG. 7 is a cross-sectional view of one embodiment of the tube 26. The tube 26 communicates with the pump 24 via the housing 52 that encloses the valve assemblies 54. In one embodiment, the valve assemblies 54 are integrated into the tube 26 and the tube is integrated seamlessly with the pump 24.

In one embodiment, the tube 26 includes a first lumen 90 separated from a second lumen 92 by a wall 94 that is internal to the tube 26. In one embodiment, the second lumen 92 includes an exposed exterior wall 96, and at least a portion 98 of the exposed exterior wall 96 is configured to expand to provide the second lumen 92 with an inflatable storage compartment 60. As one example, less than half of the circumference of the tube 26 (less than 180 degrees of the circumference of the tube 26, or approximately 90 degrees of the circumference of the exterior wall 96 of the entire tube 26) is fabricated in a manner that allows the portion 98 to expand when pressurized. This expansion feature may be achieved by providing the portion 98 of the exterior wall 96 with a thinner wall section as compared to the remainder of the exterior wall 96, as one example.

In one embodiment, the tube 26 is a single tube that is integrated to include the first lumen 90 communicating between the cuff 22 and the pump 24 and the separate second lumen 92 communicating between the cuff 22 and the pump 24. In one embodiment, the lumens 90, 92 are integrated as a monolithic one-piece assembly.

Alternatively, the expansion feature may be achieved by providing the portion 98 of the exterior wall 96 with a more flexible material (lower durometer) section as compared to the remainder of the exterior wall 96. The durometer or hardness/expandability of the portion 98 of the exterior wall 96 of the tube 26 may be selectively adjusted to achieve an appropriate amount of expansion, for example by adjusting the durometer or hardness of the portion 98 to be lower than the durometer/hardness of the remaining part of the tube 26. As one example, the portion 98 of the exposed exterior wall 96 of the second lumen 92 is fabricated from a material having a lower hardness durometer than a hardness durometer of a remaining portion of the tube 26. One suitable example provides the portion 98 of the exposed exterior wall 96 of the second lumen 92 with a durometer in a range from 10-40 Shore A hardness and the remaining portion of the tube 26 is provided with a durometer in a range from 45-90 Shore A hardness. This configures the portion 98 to expand more than the rest of the tube 26 when the lumen 92 is pressurized about the equilibrium pressure.

In one embodiment, the tube 26 is a substantially cylindrical tube and the wall 94 internal to the tube 26 is centrally located on a longitudinal diameter of the tube 26.

In one embodiment, the exterior wall 96 is provided with a first thickness T1 and the expandable portion 98 of the exposed exterior wall 96 is provided with a second thickness T2. In one embodiment, the first thickness T1 is greater than the second thickness T2, which configures the tube 26 to have a region (i.e., portion 98) that will expand/bulge in response to an increase in force, for example when the second lumen 92 is pressurized. One suitable range for the first thickness T1 of the exterior wall 96 is between about 0.035-0.100 inches. One suitable range for the second thickness T2 of the expandable portion 98 is between about 0.005-0.025 inches.

FIG. 7 illustrates one embodiment of the tube 26 section of the assembled AUS system 20 provided as a closed system and maintained at an equilibrium pressure Pe. The equilibrium pressure Pe is selected to provide a sufficient pressure to expand the cuff 22 (FIG. 1) and coapt the urethra when the AUS system 20 is in the rest state, which ensures that the user is maintained in a comfortable and continent state until s/he desires to void urine. A suitable range for equilibrium pressures Pe of the closed AUS system 20 is between about 30-80 cm of water. One suitable equilibrium pressure Pe for the AUS system 20 is about 60 cm of water.

Figure 8:
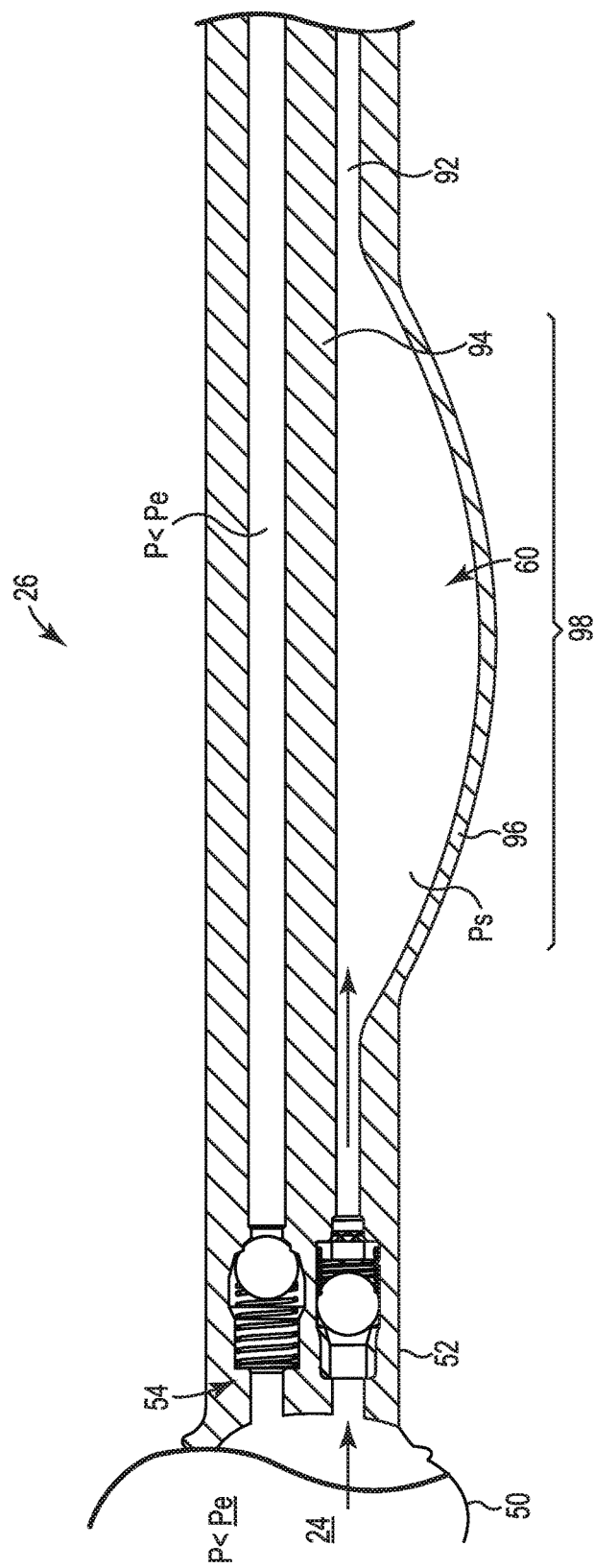
FIG. 8 is a cross-sectional view of one embodiment of the tube illustrated in FIG. 7 providing an inflatable storage compartment.

FIG. 8 illustrates one embodiment of the storage compartment 60 of the AUS system 20 maintained at a storage pressure Ps. The exposed exterior wall 96 of the second lumen 92 is configured to expand at a storage pressure Ps that is greater than the equilibrium pressure Pe, which expands the portion 98 of the wall 96 and maintains the storage compartment 60 at the storage pressure Ps. Storing the liquid from the cuff 22 in the storage compartment 60 will deflate the cuff 22, which removes pressure from the urethra and allows the user to pass urine. A suitable range for storage pressures Ps of the AUS system 20 is between about 85-120 cm of water. One suitable storage pressure Ps for the AUS system 20 is about 90 cm of water.

In one embodiment, the storage compartment 60 is sized and configured to store substantially all of the liquid volume maintained in the cuff 22 (FIG. 1). For example, when the cuff 22 is deflated by a volume V to deflate the cuff 22 and allow the user to pass urine, the storage compartment 60 expands to accept the additional volume V. Thus, the storage compartment 60 provides a storage reservoir to hold the additional volume V. The second lumen 92 is configured to expand to provide the system 20 with a pressure-regulating storage compartment.

FIG. 9 is an end view and FIG. 10 is a cross-sectional view of one end of the tube 26 that communicates with the cuff 22 (FIG. 4). As described above, a portion of the tube 26 is configured to provide a reservoir function and store a volume of liquid that is drained from the cuff 22, which allows the cuff 22 to relax or deflate, thus removing pressure applied to the urethra and allowing the user to pass urine. After the user has passed urine, it is desirable to coapt the urethra and return the user to a continent state. In one embodiment, the end of the tube 26 that communicates with the cuff 22 is provided with a bleeder valve 100 that communicates with the cuff 22. The bleeder valve 100 is configured to allow the liquid that is stored in the storage compartment 60 of the second lumen 92 to eventually transfer back into the cuff 22. In other words, the bleeder valve 100 is configured to dissipate the liquid stored in the storage compartment 60 of the second lumen 92 from the higher storage pressure Ps to the lower equilibrium pressure Pe, thus returning the system 20 to the equilibrium pressure Pe.

In one embodiment, the bleeder valve 100 is provided as a diaphragm having a small orifice 102 that is sized to allow liquid to slowly pass through the bleeder valve 100 and into the cuff 22 to equalize the pressure of the system 20 to the equilibrium pressure Pe. The bleeder valve 100 is illustrated as a diaphragm having a single orifice 102, although other forms for the bleeder valve are also acceptable. For example, an array of orifices could be provided in a diaphragm of the bleeder valve 100 that would allow the liquid in the storage compartment 60 to flow in a controlled and time-lapsed manner back into the cuff 22 and return the system 22 to its equilibrium pressure Pe.

FIG. 11A is a cross-sectional view of the AUS system 20 in a rest or equilibrium state operating to coapt a urethra U of a user. The illustrated view of FIG. 11A is not to scale. The system 20 is initially filled with a fill volume of liquid of about 40 cc and the components (cuff 22, pump 24, and tube 26) are sealed in a closed system to retain the fill volume of liquid. The closed system 20 is maintained at the equilibrium pressure Pe. Specifically, each pillow 32a, 32b, 32c of the expanding bladder 32 of the cuff 22 is maintained at the equilibrium pressure Pe, which is selected to provide a calculated and sufficient amount of pressure against the urethra U in order to close the urethra and provide the user with a continent state. The first lumen 90, the bulb 50, and the second lumen 92 are also maintained at the equilibrium pressure Pe. The second lumen 92 is sized to retain a first volume V1 of liquid when the system 20 is at equilibrium.

FIG. 11B is a cross-sectional view of the AUS system 20 in an activated state configured to allow the urethra U of the user to open and pass urine. The illustrated view of FIG. 11B is not to scale. The system 20 has been activated to move away from the equilibrium state, for example by pumping the bulb 50 of the pump 24 to move liquid out of the cuff 22 and into the storage compartment 60. In the activated state, the pillows 32a, 32b, 32c of the cuff 22 have been deflated by moving liquid out of the cuff 22, through the pump 24, and into the storage compartment 60. The urethra U opens to allow the urethra U to pass urine. The pump 24 pressurizes the liquid in the second lumen 92/storage compartment 60 to the storage pressure Ps. The portion 98 of the second lumen 92 expands and stores the liquid that was removed from the cuff 22. The storage pressure Ps is greater than the equilibrium pressure Pe. The portion 98 of the exterior wall 96 of the second lumen 92 is configured to expand when exposed to the storage pressure Ps. The evacuation of the liquid out of the cuff 22 and into the storage compartment 60 results in a pressure P1 of the first lumen 90 that is lower than the equilibrium pressure Pe and the storage pressure Ps.

In one embodiment, the storage compartment 60 of the second lumen 92 has a storage volume V2 that is greater than the first volume V1 of the at-rest/equilibrium state of the second lumen 92. In one embodiment, the first lumen 90 and the second lumen 92 each have approximately equal volumes when the system 20 is maintained at the equilibrium pressure Pe. In one embodiment, the second lumen 92 has a first volume V1 at the equilibrium pressure Pe and the second lumen 92 has a second volume V2 at the storage pressure Ps that is approximately twice the first volume V1. In one embodiment, the second lumen 92 has a first volume V1 at the equilibrium pressure Pe and the second lumen 92 has a second volume V2 at the storage pressure Ps that is more than twice the first volume V1. For example, the second lumen 92 has a second volume V2 at the storage pressure Ps that is three times, or four times, or 3-6 times the first volume V1

With reference to both FIG. 11A and FIG. 11B, the cuff 22 is configured to coapt the urethra U when the system 20 is at the equilibrium pressure Pe, and the exposed exterior wall 96 of the second lumen 92 is configured to expand at the storage pressure Ps (Ps is greater than Pe) to store the liquid that has been removed from the cuff 22. The movement of the liquid out of the cuff 22 and into the storage compartment 60 lowers the pressure and the cuff 22, which allows the urethra U to open and pass urine.

With reference to FIG. 11B, the liquid volume V2 maintained in the storage compartment 60 will eventually pass through the bleeder valve 100 and flow back into the cuff 22. The bleeder valve 100 is configured to allow the system 20 to return to the equilibrium pressure Pe over a period of time of several minutes, but less than about one hour, which returns the user to the continent state.

FIG. 11A illustrates the cuff 22 inflated at the equilibrium pressure Pe with a cuff volume of liquid that functions to selectively close the urethra U for treatment of urinary incontinence.

FIG. 11B illustrates the pump operated to move the cuff volume of liquid out of the cuff 22 to provide the cuff 22 with a deflated state that allows the urethra U to open and pass urine. The storage compartment 60 of the second lumen 92 retains the cuff volume of liquid. The single tube 26 is configured to store the energy of the closed system, including the energy maintained at the equilibrium pressure Pe and the energy when the storage compartment 60 is pressurized to the storage pressure Ps.

The system 20 is designed to provide a closed system with an equilibrium pressure Pe selected to provide a sufficient pressure to coapt the urethra when the AUS system 20 is in the rest state, which ensures that the user is maintained in a comfortable and continent state until s/he desires to void urine. A suitable range for equilibrium pressures Pe of the closed AUS system 20 is between about 30-80 cm of water. One suitable equilibrium pressure Pe for the AUS system 20 is about 60 cm of water. The storage compartment 60 is configured to expand at a storage pressure Ps that is greater than the equilibrium pressure Pe as the cuff 22 is deflated. A suitable range for storage pressures Ps of the AUS system 20 is between about 85-120 cm of water. One suitable storage pressure Ps for the AUS system 20 is about 90 cm of water.

The system 20 includes the conduit 26 that is a pressure-regulating liquid storage reservoir 26. At least a portion of the pressure-regulating liquid storage reservoir 26 is pressurizeable to a pressure above the steady-state equilibrium pressure of the system. The pressure-regulating liquid storage reservoir 26 includes the storage compartment 60 that inflates to hold the volume of liquid moved from the cuff 22, and after holding the increased pressure allows the system 20 to regulate back to the equilibrium pressure by allowing liquid to flow through the bleeder valve 100.

In contrast to other AUS systems that have a cuff and a pressure-regulating balloon, the system 20 includes a conduit 26 that plays the role of a pressure-regulating balloon by holding the volume of liquid that acted to coapt the urethra (the liquid in the cuff 22).

Figure 12A:
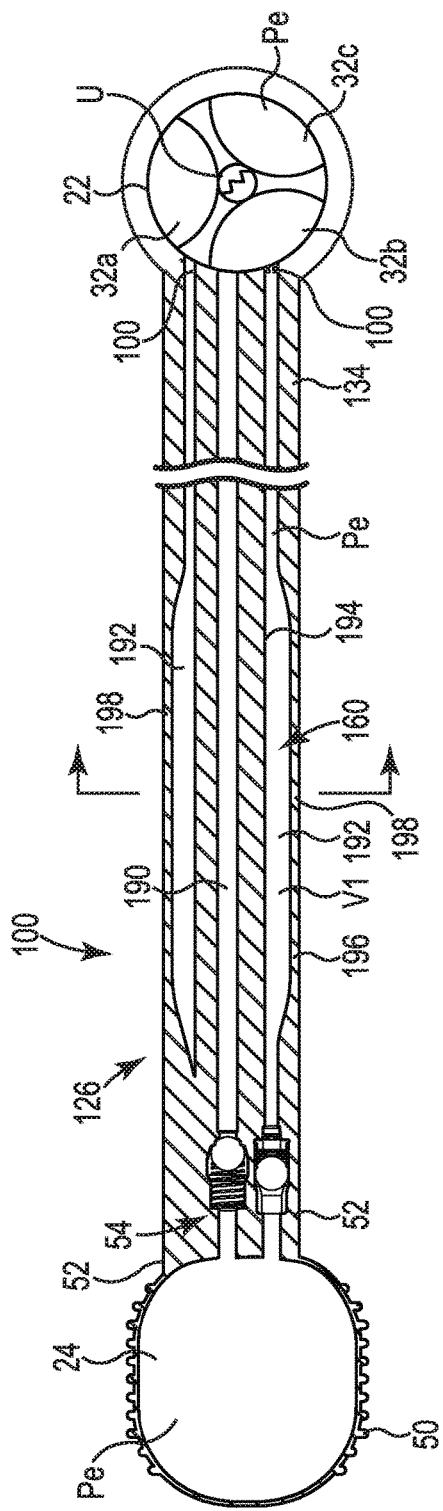
FIG. 12A is a longitudinal cross-sectional view and FIG. 12B is a lateral cross-sectional view of one embodiment of an artificial urinary sphincter (AUS) system.

FIG. 12A is a cross-sectional view of one embodiment of an AUS system 100 including a tube 126 that provides the system 100 with a pressure-regulating liquid storage reservoir. The tube 126 communicates with the pump 24 described above via the housing 52 that encloses the valve assemblies 54. The tube 126 is attached to the cuff 22 described above. In one embodiment, the tube 126 includes a first lumen 190 that is provided to remove liquid from the cuff 22 and a second lumen 192 that circumferentially surrounds the first lumen 190. The first lumen 190 is separated from the second lumen 92 by a wall 194 that is internal to the tube 126.

Figure 12B:
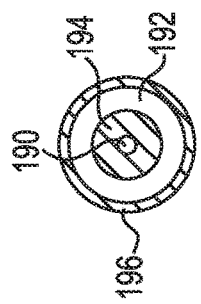

FIG. 12B is a cross-sectional view of the tube 126 taken through a central portion of the second lumen 192. In one embodiment, the second lumen 192 includes an exposed circumferential exterior wall 196, and at least a portion 198 of the exposed exterior wall 196 is configured to expand to provide the second lumen 192 with an inflatable and pressure-regulating liquid storage compartment 160. In this embodiment, an outer circumferential compartment 160 surrounds 360 degrees of the tube 126. That is, the second lumen 192 circumferentially surrounds the first lumen 190.

In one embodiment, the system 20 is provided as a kit of parts to a surgeon or clinic/hospital facility for the treatment of urinary incontinence. The kit of parts is provided with documentation or instructions for use describing and reviewing the surgical procedure by which the surgeon has been trained for implantation of the system 20.

The kit of parts is provided in a package to treat urinary incontinence and includes the cuff 22 that is sized for placement around the urethra U, a pump 24 that is sized to move liquid out of the cuff 22, and a tube 26 that is attachable between the cuff 22 and the pump 24. The tube 26 is fabricated to include a first lumen 90 and a second lumen 92 that both communicate between the cuff 22 and the pump 24, as described above. At least a portion 98 of the exposed exterior wall 96 of the second lumen 92 is fabricated to expand to provide the second lumen 92 with an inflatable storage compartment 60. The inflatable storage compartment 60 is sized to receive and store the volume of liquid that is transferred out of the cuff 22 when the cuff 22 is deflated (i.e., when the user passes urine).

A method of treating a patient suffering from urinary incontinence with the system 20 includes a surgical procedure to implant the system 20. The patient is prepared for surgery in a manner described by the hospital or clinic policies or as supervised and approved by the surgeon. The perineal area of the patient is cleaned with suitable cleansers and prepared for surgery. A perineal incision is made on the midline of the patient, and tissue is dissected to expose the bulbospongiosus muscle supporting the urethra U. The surgeon will dissect laterally to free the fascia around the bulbospongiosus muscle and expose a portion of the bulbar urethra U. The bulbospongiosus muscle is immobilized, for example by clamping laterally to each side of the patient, which exposes the urethra for access by the surgeon. The surgeon dissects additional tissue and muscle by "tunneling" around the posterior side of the urethra to create a pathway around a circumference of the urethra. The cuff 22 is traversed along the pathway around the urethra U until a portion of the cuff 22 is posterior to the urethra U with the tab 36 and a slot 42 of the cuff 22 anterior to the urethra U. The tab 36 is inserted into the slot 42 to secure the cuff 22 around the urethra U.

The surgeon typically confirms performance of the cuff 22 by injecting liquid into the connector 34 or the system 20, usually immediately prior to implantation of the system 20. The tube 26 and the pump 24 are subsequently attached to the cuff 22. For example, the pump 24 is located in the scrotum (male) or labia (female) of the user and the tube 26 is connected between the pump 24 and the cuff 22 that has been placed around the urethra U. The surgeon will pressurize the system 20 to the equilibrium pressure Pe and cause the cuff 22 to coapt the urethra U. The surgeon will confirm that operation of the pump 24 will remove liquid from the cuff 22, thus opening the urethra U and allowing the patient to pass urine. The surgical site is closed after confirmation of performance of the system 20.

Embodiments of treating urinary incontinence include fabricating the tube 26, 126 to include a first lumen separated from a second lumen by a wall internal to the tube; and fabricating at least a portion of an exposed exterior wall of the second lumen to expand to provide the second lumen with an inflatable storage compartment; and providing to a surgeon instructions for use on implantation of the device.

Embodiments of treating urinary incontinence include connecting a first end of the pressure-regulating storage compartment tube 26, 126 to the cuff 22 and connecting a second end of the pressure-regulating storage compartment tube 26, 126 to the pump 24.

Embodiments provide a "fail-safe" system 20 that is implanted into the patient and maintained at the equilibrium pressure Pe. In the event that the system 20 develops an undesirable leak, the system 20 will de-pressurize to a pressure of less than the equilibrium pressure Pe, which will result in the cuff 22 deflating to allow the urethra to open. Thus, in the event that the system 20 experiences a non-steady state event, the cuff 22 opens to allow the user to pass urine.

Embodiments of the artificial urinary sphincter (AUS) system described above include a fully functional system for treating urinary incontinence that operates in the absence of a reservoir provided separate from the tubing, cuff, and pump. The tube or tubing is connected between the cuff and the pump and includes a lumen that is configured to expand to provide the lumen/system with an inflatable storage compartment.

Although specific embodiments have been illustrated and described in this patent application, it will be appreciated by those of ordinary skill in the art that a variety of alternate and/or equivalent implementations may be substituted for the specific embodiments shown and described without departing from the scope of the invention. This patent application is intended to cover any adaptations or variations of medical devices, as discussed above. Therefore, it is intended that this invention be limited only by the claims and their equivalents.

What is claimed is:

1. A method of treating urinary incontinence, the method comprising:
    providing a device to treat urinary incontinence including a cuff configured to coapt a urethra of a patient, a pump, and a tube attachable between the cuff and the pump;
    providing the tube with a first lumen separated from a second lumen by a wall internal to the tube;
    providing at least a portion of an exposed exterior wall of the second lumen to expand to provide the second lumen with an inflatable storage compartment;
    providing to a surgeon instructions for use on implantation of the device;
    implanting the cuff around the urethra of the patient, implanting the pump into one of a labia and a scrotum of the patient, connecting the tube between the cuff and the pump, and implanting the tube into the body of the patient by extending the tube including the second lumen out from one of the labia and the scrotum to the cuff around the urethra.

2. The method of claim 1, comprising providing the second lumen of the tube as a pressure-regulating storage compartment.

3. The method of claim 2, comprising connecting a first end of the pressure-regulating storage compartment to the cuff and connecting a second end of the pressure-regulating storage compartment to the pump.

4. The method of claim 1, further comprising operating the pump, moving liquid out of the cuff, and adapting the urethra to open allowing the urethra to pass urine.

5. The method of claim 1, wherein implanting the pump into one of the labia and the scrotum of the patient includes implanting the pump into the scrotum after forming a perineal incision.

6. The method of claim 1, wherein extending the tube includes extending the second lumen inside of a pelvis of the patient to the cuff.

7. A method of treating urinary incontinence, the method comprising:
    providing a cuff, a pump, and a single tube integrated to comprise a first lumen communicating between the cuff and the pump and a separate second lumen communicating between the cuff and the pump, with the separate second lumen separated from the first lumen by a wall where the single tube contacts the cuff;
    implanting the cuff around a urethra of a patient, implanting the pump into one of a scrotum and a labia located external a pelvis of the patient, connecting the single tube between the cuff and the pump and implanting the single tube into the body of the patient including extending the first lumen and the separate second lumen from the pump to a location inside of the pelvis distal a bladder of the patient;
    configuring the cuff to inflate with a cuff volume of liquid that is selected to constrict the cuff around the urethra of the patient in treating urinary incontinence;
    operating the pump and moving the cuff volume of liquid out of the cuff, thus deflating the cuff and reducing constriction of the cuff around the urethra; and
    providing an opening between the second lumen and the cuff, with the opening adapted for allowing the cuff volume of liquid to flow out of the second lumen, through the opening, and into the cuff.

8. The method of claim 7, comprising adapting the second lumen to expand, thus providing the single tube with an expandable storage compartment sized to retain the cuff volume of liquid.

9. The method of claim 7, comprising forming the first lumen in longitudinal side-by-side alignment with the second lumen.

10. The method of claim 7, comprising providing a bleeder valve between the second lumen and the cuff, and configuring the bleeder valve to allow the liquid to flow out of the second lumen and into the cuff.

11. The method of claim 7, comprising adjusting a first pressure in the second lumen and constricting the cuff around the urethra of the patient.

12. The method of claim 11, comprising adjusting a second pressure in the second lumen to be greater than the first pressure and expanding the second lumen and reducing constriction of the cuff around the urethra.

13. The method of claim 7, comprising adjusting the second lumen to have a first volume measured at an equilibrium pressure and configuring the second lumen to have a second volume measured at a selected storage pressure, where the second volume is approximately twice the first volume.

* * * * *